US009039665B2

(12) United States Patent
Bodenlenz et al.

(10) Patent No.: US 9,039,665 B2
(45) Date of Patent: May 26, 2015

(54) FILAMENT-BASED CATHETER

(75) Inventors: Manfred Bodenlenz, Graz (AT); Christian Hoefferer, Graz (AT); Thomas Birngruber, Graz (AT); Lukas Schaupp, Graz (AT)

(73) Assignee: Joanneum Research Forschungsgesellschaft MBH, Graz (AT)

( * ) Notice: Subject to any disclaimer, the term of this patent is extended or adjusted under 35 U.S.C. 154(b) by 1075 days.

(21) Appl. No.: 13/119,527

(22) PCT Filed: Sep. 9, 2009

(86) PCT No.: PCT/EP2009/006543
§ 371 (c)(1),
(2), (4) Date: May 31, 2011

(87) PCT Pub. No.: WO2010/031515
PCT Pub. Date: Mar. 25, 2010

(65) Prior Publication Data
US 2011/0224628 A1 Sep. 15, 2011

(30) Foreign Application Priority Data
Sep. 17, 2008 (EP) .................................. 08016402

(51) Int. Cl.
*A61M 25/00* (2006.01)
*A61M 27/00* (2006.01)
(52) U.S. Cl.
CPC ............ *A61M 27/00* (2013.01); *A61M 25/0012* (2013.01); *A61M 25/0026* (2013.01); *A61M 25/0043* (2013.01); *A61M 2025/0057* (2013.01)

(58) Field of Classification Search
CPC ................. A61M 2025/0057; A61M 25/0012; A61M 25/0026; A61M 25/0043; A61M 27/00
USPC .......................... 604/264, 523, 104, 163, 500
See application file for complete search history.

(56) References Cited

U.S. PATENT DOCUMENTS

| | | | |
|---|---|---|---|
| 4,767,400 A | 8/1988 | Miller et al. | |
| 4,921,484 A | 5/1990 | Hillstead | |
| 5,498,251 A | 3/1996 | Dalton | |
| 6,361,545 B1 * | 3/2002 | Macoviak et al. ............ 606/200 |
| 8,177,775 B2 * | 5/2012 | Kunst ......................... 604/890.1 |
| 2004/0168934 A1 * | 9/2004 | Schaupp et al. ........... 205/777.5 |

FOREIGN PATENT DOCUMENTS

| | | |
|---|---|---|
| EP | 0474870 A1 | 3/1992 |
| EP | 0511499 A2 | 11/1992 |
| WO | 9111209 A1 | 8/1991 |

(Continued)

*Primary Examiner* — Kami A Bosworth
*Assistant Examiner* — Imani Hayman
(74) *Attorney, Agent, or Firm* — Robert A. Blaha; Smith Risley Tempel Santos LLC

(57) ABSTRACT

A membrane-free perfusion catheter comprising an exchange surface having a filament structure, a delivery unit for delivery of perfusion fluid to a lumen of the filament structure in a manner to allow for an exchange of substances between a medium surrounding the lumen and the perfusion fluid via the filament structure, and a drain unit for draining the medium surrounding the exchange surface and/or for draining the perfusion fluid delivered to the lumen of the filament structure after the exchange of substances between the medium surrounding the lumen and the perfusion fluid via the filament structure.

19 Claims, 7 Drawing Sheets

(56) References Cited

FOREIGN PATENT DOCUMENTS

| WO | 9200113 | A1 | 1/1992 |
| WO | 0103763 | A1 | 1/2001 |
| WO | 0197896 | A1 | 12/2001 |
| WO | 2006037336 | A1 | 4/2006 |
| WO | 2007131780 | A1 | 11/2007 |

* cited by examiner

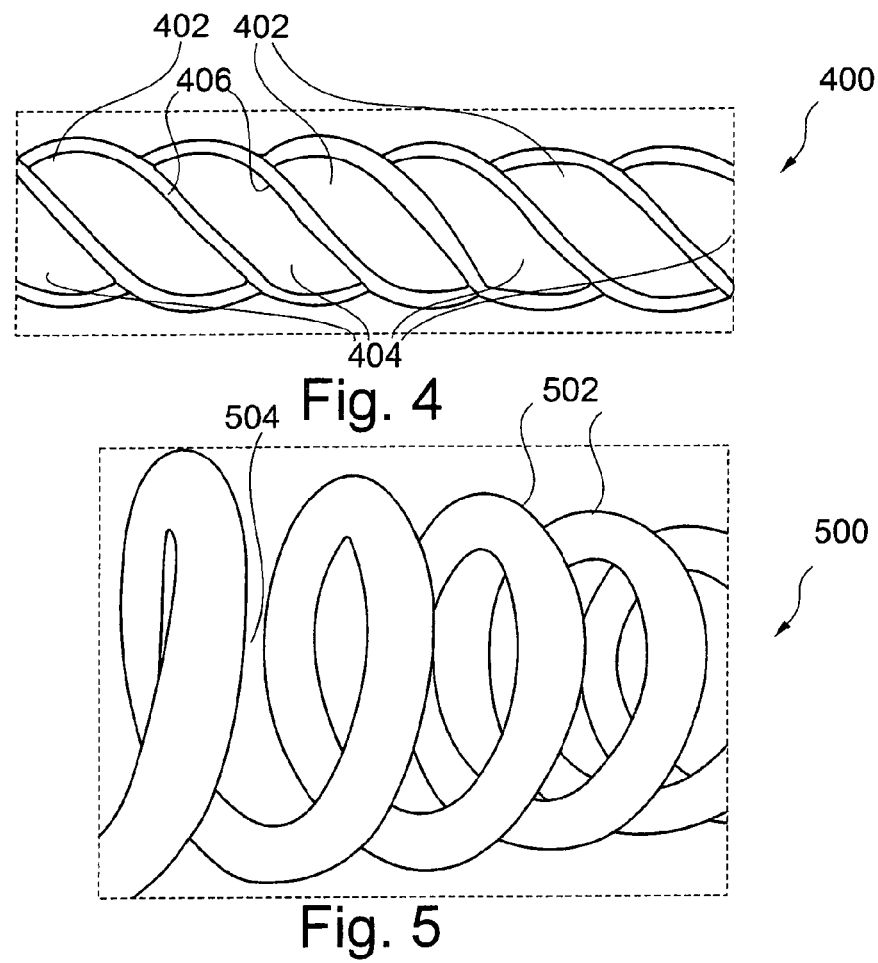
Fig. 4
Fig. 5
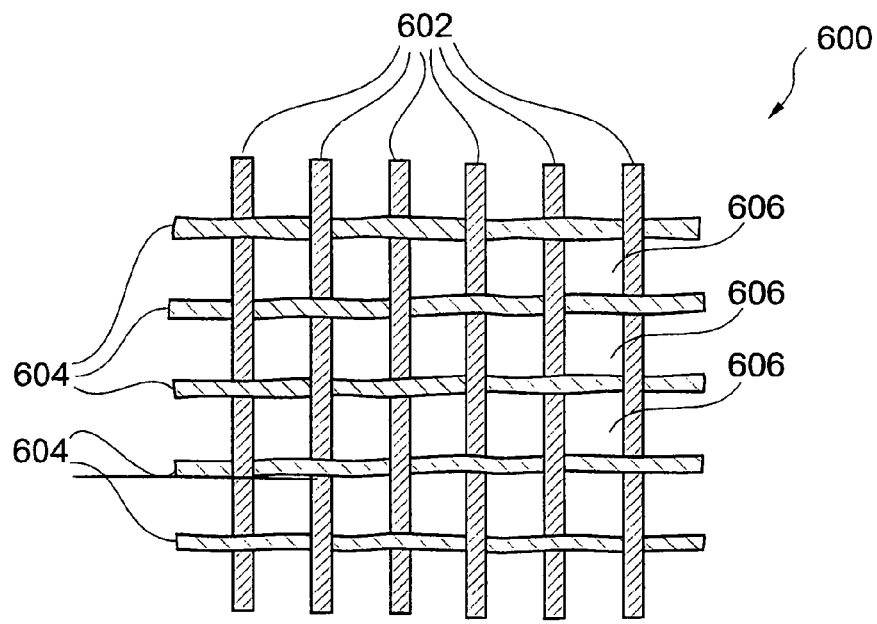
Fig. 6

FILAMENT-BASED CATHETER

This application claims the benefit of the filing date of European Patent Application No. 08016402.3 filed Sep. 17, 2008, the disclosure of which is hereby incorporated herein by reference.

The invention relates to a catheter.

Moreover, the invention relates to a method of manufacturing a catheter.

Beyond this, the invention relates to a method of operating a catheter.

Furthermore, a method of using a catheter is provided.

WO 2001/097896 A1 discloses a drainage catheter adapted to drain fluid from the body cavity through a body conduit and includes an elongate tube having a distal end and a retention member disposed at the distal end and adapted for movement between the low-profile state facilitating insertion of the catheter and a high-profile state facilitating the tension of the catheter in its operative position. A woven mesh forms at least a portion of one of the tube and the retention member, and can be made permeable or impermeable in various regions of the catheter. The woven mesh can be formed of filaments heat-settable so that the catheter automatically moves to the high-profile state. Insertion of the catheter can be facilitated using an obturator and a guidewire in an associated method, an obturator facilitating insertion of the catheter can be removed to permit the catheter to automatically return to a normal, high-profile state U.S. Pat. No. 4,921,484 discloses a mesh balloon catheter device which includes a catheter having a distal end and a proximal end, a tube of woven interlaced filaments forming a tubular mesh and having a proximal end connected to the distal end of the catheter and a distal end, a flush tube or fiber optic tube extending through the catheter and the tubular mesh and fixed to the distal end of the tubular mesh, and a mechanism for moving the distal end of the tubular mesh toward the proximal end of the tubular mesh to cause the tubular mesh to balloon laterally outwardly to the shape of a mesh balloon. The moving mechanism can be realized by the flush tube or fiber optic tube connected to the distal end of the tubular mesh or by a control wire connected to the distal end of the tubular mesh and extending through the catheter WO 2006/037336 A1 discloses a medical device such as a catheter, and a method for making such a device. In particular, a medical device is disclosed comprising a tip, a drainage section and a retention section extending between the drainage section and the tip, the retention section comprises a plurality of first drainage passages defined between cross braided filaments of the retention section and is in fluid communication with the drainage section. More specifically, a medical device is provided wherein at least one of the tip and the retention section defines one or more second drainages passage, said second drainages passage being in fluid communication with the drainage section, a cross-sectional area of the second drainage passage being larger than a cross-sectional area of any one of the first drainage passages which are adjacent to the second drainage passage.

DE 69125476 T2 discloses a catheter to be used for the movement of fluids having means for maintaining the position of that catheter within a preselected location in the body. The device comprises an elongated flexible tubular member with a longitudinally extending lumen through it. An axially and radially elastically extensible, foraminous woven tube having two ends is disposed between the end of the tubular member and a tip, the tip being spaced from the tubular member. The foramina of the woven tube allow the free flow of fluids therethrough. The woven tube is translatable between three configurations: relaxed, extended and over-center. In the relaxed configuration the woven tube has predetermined length and a predetermined diameter, the predetermined diameter which is greater than the outer diameter of the tubular member and preferably an ovoid shape. In the extended configuration the woven tube has a length that is greater than the predetermined length, and further wherein when in the extended configuration, the outer diameter of the woven tube can assume a generally cylindrical shape. In the third configuration, the woven tube assumes an overcenter shape where it is doubled back on itself to form a cup- or disc-like shape.

EP 1202770 discloses a microdialysis probe, which comprises a dialysis membrane located and supported between a closed distal end of the probe and a proximal end of the same, which membrane essentially surrounding a space for passage of perfusion liquid; said probe having inlet and outlet means for perfusion liquid. The probe exhibits a deformable mesh sleeve adapted to enclose and protect at least the dialysis membrane, the proximal end of the deformable being fastened to the probe between the proximal end of the probe and the dialysis membrane.

U.S. Pat. No. 5,498,251 discloses a tissue perfusion catheter which includes a tightly wound coil spring having an exterior, fluid impervious sleeve extending from a proximal end up to a distal portion of the spring which terminates at a sealed distal tip. Connection of the proximal end of the catheter to a source permits perfusion of diseased tissue with a therapeutic fluid which oozes at a low rate from the unsealed distal portion, while avoiding tissue ingrowth tending to plug the catheter.

Perfusing may denote permeating something, particularly with a liquid. Perfusion may denote the introduction of a drug or nutrients in order to reach an internal organ or tissues.

It is an object of the invention to provide an efficient catheter.

In order to achieve the object defined above, a catheter, a method of manufacturing a catheter, a method of operating a catheter, and a method of using a catheter according to the independent claims are provided.

According to an exemplary embodiment of the invention, a catheter may be provided comprising an exchange surface having a filament structure (for instance existing exclusively of the filament structure), and a drain unit for draining (for instance by sucking) a medium surrounding the exchange surface or for draining a perfusion fluid delivered to a lumen of the filament structure after an exchange of substances between a medium surrounding the lumen and the perfusion fluid via the filament structure.

According to another exemplary embodiment of the invention, a method of manufacturing a catheter is provided, the method comprising forming an exchange surface of the catheter based on a filament structure, and coupling a drain unit to the filament structure for draining a medium surrounding the exchange surface or for draining a perfusion fluid delivered to a lumen of the filament structure after an exchange of substances between a medium surrounding the lumen and the perfusion fluid via the filament structure.

According to still another exemplary embodiment of the invention, a method is provided, wherein the method comprises the steps of (providing) a catheter having the above-mentioned features, optionally inserting the catheter into a physiological object (alternatively using the catheter for an in vitro application or any other non-physiological application) and draining the medium surrounding the exchange surface or draining the perfusion fluid delivered to the lumen of the filament structure after the exchange of substances between the medium surrounding the lumen and the perfusion fluid via the filament structure.

According to yet another exemplary embodiment of the invention, a catheter having the above mentioned features is used for measuring at least one physiological parameter in a physiological object (or alternatively may be used for in vitro applications).

The term "catheter" may particularly denote a tube (or any differently shaped geometrical structure) that can be inserted into a body, wherein upon inserting the catheter into the body, the catheter may generate itself a cavity in which the catheter is accommodated. Catheters may thereby allow access by surgical instruments. A catheter may be a flexible tube. In other embodiments, a catheter may be a stiff tube. Its diameter may vary particularly between 0.2 mm and 10 mm.

In an embodiment, an "exchange surface" of a catheter according to an exemplary embodiment of the invention has—compared to sizes of macromolecules—large macroscopic openings (that is openings with dimensions larger than typical freely moving macromolecules in an organism such as a human or animal organism) between adjacent filament sections. Thus, the permeability of such an exchange surface does not distinguish between small molecules capable of passing the exchange surface and large molecules being also capable of passing the exchange surface. In other words, a catheter according to an exemplary embodiment may advantageously lack a molecular cut-off so that the exchange efficiency may be very high also for large molecules and such with high affinity for instance to proteins or surfaces. There may be no size-limitation regarding molecules being capable to pass the exchange surface. An exchange surface according to such an embodiment may be free of a size-based filter function for moving macromolecules in the physiological subject. Even individual migrating large cells (such as immune cells) may be capable of traversing the exchange surface. An exchange surface according to an embodiment may serve as a tissue supporting wall having holes of a size which only prevent tissue from growing into or invading the lumen thereby preventing clogging and simultaneously being safe and tear proof. A catheter according to an exemplary embodiment of the invention having such an exchange surface may be membrane-free. Such a membrane-free catheter may have an exchange surface with a deterministic, well-defined size of pores.

In contrast to such an exchange surface, a "membrane" may particularly denote a semi-permeable statistically defined diffusion barrier through which substances of a sufficiently small size can diffuse easily, but substances having a larger size can not. Thus, a membrane may act as a statistical filter that allows rather efficient passage up to a given molecular size ('Cut-Off' value), but rejects larger molecules from passing. Thus, a material exchange with a statistically defined molecular cut-off can be achieved via the membrane. Membranes may selectively control mass transport between the phases or environments, since they may be permeable for a first group of materials and impermeable for a second group of materials.

Hence, an exchange surface of a catheter according to an embodiment of the invention can be denoted as membrane-free.

The term "filament" may particularly denote any wire, fiber, thread or yarn or any other oblong structure which is sufficiently flexible to be bendable for forming any desired shape, for instance a tubular shape, including the formation of loops between different filament sections. A filament may be denoted as a very thin rope which can be interwoven with other filaments or which allows interweaving between different filament portions. An individual filament may be combined with other filaments to spin larger structures such as multi-filament yarns or threads and/or plane like or multi-dimensional (for instance two- or three-dimensional) structures such as tubes or spheres. Such a filament may be an oblong structure, for instance an essentially cylindrical structure having a very small diameter (for instance of less than 200 μm, particularly less than 100 μm) and a very long length (for instance longer than 1 cm, particularly longer than 5 cm). Thus, a filament may be a small dimensioned fiber having a large aspect ratio, for instance larger than 100. The dimension of the holes or gaps in the catheter according to an exemplary embodiment may have a dimension of 50 μm to 500 μm. For instance, filaments used for forming the exchange surface may be flat filaments (which may have an oval or rectangular cross-section) or may have a circular or square cross-section. The exchange surface may be formed of filaments along an entire extension of the exchange surface. In other words, the exchange surface may be free of sections which are not formed by one or more filaments. And the filaments may extend from the exchange surface into the wall of the impermeable parts of the catheter structure.

The term "wound filament structure" may particularly denote a structure formed on the basis of one or more filaments (which may be a wire made of a metallic material or a filament made of a non-metallic material) which is wound for instance to form some kind of helix.

The term "braiding" may particularly denote an interweaving or twinning of two, three or more separate strands in a diagonally overlapping pattern. The strands may be of one or more materials. Braids can be flat or tubular.

The term "coiling" may particularly denote a single flat or tubular strand wound to form a helical structure. In a coiled configuration, one or more coils having parallel windings may be provided.

The term "braided tubing" or "helical tubing" may particularly denote braidings or coilings integrated within a tube or a tube's wall.

The term "mesh" may particularly denote a fabric or a web having many connected or weaved pieces. A mesh may be made of a plastic material such as but not limited to polypropylene, polyethylene, nylon, PVC or PTFE. A metal mesh can be woven, welded, expanded, photochemically etched or electroformed from steel or other materials.

The term "physiological object" or biological object may particularly denote any human being, any animal, and any plant (any organism).

The term "impermeable" may particularly denote a material property of a component, namely that the component cannot be traversed—in any significant manner or quantity—by fluidic or solid particles. In contrast to this, holes in the exchange surface may be permeable for substances.

The term "flexible" may particularly denote a material property of the tube, namely that the tube can be reversibly deformed under the influence of an external force having an order of magnitude of a muscle force of a human being. The term "biocompatible" may particularly denote a material property of a substance, namely that the substance, when inserted in living tissue, does not harm or negatively influence the physiological conditions at such a location in a body.

The term "physiological parameter" may particularly denote any parameter which is related to the physiology of a living organism, for instance the metabolism, etc. Such a physiological parameter may include the concentration of a hormone, a protein concentration, etc.

The term "physiologically active substance" may particularly denote any substance which may have an effect on the physiology of the living organism, for instance a medication, a drug, etc.

The term "physiologically inert substance" may particularly denote any substance which may be free of causing any effect on the physiology of a living organism, for instance mannitol, inulin under isotonic conditions, etc.

The term "structure" may denote any piece of material based on which a catheter may be built. It may be a planar structure, a three-dimensional structure, etc. Examples are tubes, circles, polygons.

In the context of this description, the term "perfusion" may particularly denote a continuous supply of perfusion fluid to one section of a catheter channel or filament-based exchange surface (which may define a closed, for instance circumferentially closed, exchange area or web) while simultaneously draining perfusion fluid enriched by one or more substances from a medium surrounding the filament-based exchange surface at another section of the catheter channel or of the filament-based exchange surface. For example, the perfusion catheter may be inserted into a tissue of a physiological object such as a patient. The tissue may then deliver some of its interstitial fluid or substances to the perfusion fluid. A bidirectional exchange of substances is possible via the exchange surface of the filament structure.

The term "perfusion fluid" may particularly denote a fluid (such as a buffer, water, a medication, etc.) which may be brought in interaction with a body fluid/fluidic sample/tissue via the exchange surface so that a material transport from the body fluid/fluidic sample/tissue to the perfusion fluid (or vice versa) may allow to analyze a component of the body fluid/fluidic sample/tissue by analyzing the perfusate. The term "perfusion fluid" may denote the liquid entering and leaving a lumen of the catheter, respectively.

According to an exemplary embodiment, a catheter structure is provided having an exchange surface made of a filament structure. Thus, wound filaments or filament portions may be cross-linked or interconnected or attached/aligned to one another in such a manner that macroscopic and/or microscopic holes are formed between the network of filament portions serving as permeable regions, whereas the solid structure of the filaments may be impermeable. Thus, by adjusting the cross-linking properties or alignment properties of the filament portions, it may be possible to flexibly adjust the size of the openings in a deterministic manner, thereby allowing to properly design the material exchange properties of the exchange surface of the catheter. Thus, such a catheter does not have to include a porous material, i.e. an essentially two-dimensional impermeable substrate in which a plurality of statistical pores are formed, but in contrast to this an interwoven structure of essentially one-dimensional filaments may define the material exchange properties. The cross-linking of the filament components may be adjusted in such a manner that it is still possible for the different filament portions to slightly move relative to one another limited by friction, so that a particularly flexible catheter may be provided which offers great advantages for instance when inserting such a catheter into a physiological object such as human being. The flexibility may, in this context, be used for contracting the catheter selectively during inserting it into a physiological body.

Such a filigree structure may allow that basically the entire exchange surface surrounded by tissue may contribute to the exchange by mechanisms such as convection and/or diffusion. Thus, no blind portions remain which do not contribute to the material exchange. In the case of a flexible lattice, the ratio between active surface and volume may be improved (for instance by elongating the web). Thus, the exchange efficiency may be improved.

The delivery unit may supply perfusion fluid to (for instance a lumen of) the structure in a manner to allow for an exchange of substances between a surrounding medium (such as tissue of a physiological subject) and the perfusion fluid (that is from the tissue to the perfusion fluid, and/or in the opposite direction) via the filament net. The drain unit may be provided for draining the perfusion fluid after the exchange of substances between the tissue and the perfusion fluid via the holes of the filament structure.

In some embodiments, a delivery unit may be omitted and pure tissue fluid may be withdrawn from tissue using the drain unit. Hence, the delivery unit is optional. In contrast to conventional approaches, the inventive catheter design may make it possible to directly obtain undiluted tissue fluid (medium surrounding the exchange surface or lumen) by merely sucking even without the use of perfusion fluid. In such an embodiment, a delivery unit may be dispensable.

Next, further exemplary embodiments of the catheter will be explained. However, these embodiments also apply to the method of manufacturing a catheter, to the method of operating a catheter and to the method of use.

In an embodiment, the exchange surface is defined or formed by the filament structure. In other words, small channels between adjacent filaments or filament portions allow the passage of sufficiently small particles through these channels in either direction and hence through the filament structure. The exchange surface may consist of the filament structure, i.e. the filament structure alone provides the permeability between an interior and an exterior of the catheter. The filament structure therefore serves as a substitution for a membrane for particle exchange, so that no separate membrane is used or required. Consequently, such a catheter may not suffer from limitations with regard to a molecular cut-off. The catheter may therefore be denoted as a membrane-free catheter. Therefore, the exchange surface may consist of the filament structure, i.e. may include no further component such as a separate membrane. The catheter may be configured such that the filament structure alone provides for an exchange of substances between the perfusion fluid and the medium surrounding the catheter. The exchange surface can therefore integrally formed as the filament structure or may even be a single material exchange surface. The exchange surface between an interior lumen and an exterior environment of the catheter may be exclusively formed by a filament structure, i.e. without any further component contributing to the exchange function. Thus, a single-layer exchange surface may be provided by the filament structure. The catheter may be configured so that an interior of the lumen and an exterior of the lumen is separated exclusively by the wound filament layer. In other words, interior and exterior may be separated by a single homogeneous layer only, i.e. no further component is arranged between an interior of the lumen and an exterior of the lumen in such an embodiment.

The mesh size, i.e. a one dimensional extension of the gaps formed between the filaments, may be smaller than 15000 μm, particularly may be smaller than 500 μm. In different dimensions (i.e. spatial directions being perpendicular to one another), the mesh size may be the same or may be different.

The mesh size, i.e. a one dimensional extension of the gaps formed between the filaments, may be larger than 1 μm, particularly may be larger than 10 μm. For instance, the mesh size may be about 100 μm or about 50 μm (but may also be larger or smaller). A mesh size of fpm would correspond to a cut-off of about 5000 kDa which is large enough to allow practically each freely moving molecule in the body and already movable cells and bacteria to pass.

In an embodiment, a catheter is provided which includes the following:

1. a delivery unit for delivering perfusion fluid to the exchange area
2. a drain unit for draining the enriched perfusion fluid away from the exchange area
3. delivery unit and draining unit are not localized at the same position of the exchange area (but may by spaced from one another with the exchange area in between), because otherwise the perfusion fluid would not flow along the exchange area (to cause the desired exchange of substances there), but would flow directly to the drain (without sufficient exchange). Hence, the exchange area may space the delivery zone with regard to the drain zone.

In order to achieve this, a controlled flow of perfusion fluid can be provided. This may be achieved by a pump which controls the delivery of the perfusion fluid (the drain is then performed in a passive way). Alternatively, the pump may control the drain of the enriched perfusion fluid (the delivery from a delivery container is then performed in a passive way). Further alternatively, the pump defines both flows (delivery flow and drain flow) which is possible, for instance, using a two-channel peristaltic pump and two pump tubes.

The filament structure may be adapted in such a manner that filament material of the filament structure is impermeable (for physiological fluids) and gaps between adjacent portions of the filament material are permeable (for physiological fluids). By adjusting the size of the gaps or interspaces between the impermeable filament material sections, the substance exchange properties of the catheter may be set in accordance with a required application.

The filament structure may comprise a single (i.e. exactly one) filament having cross-linked filament portions. Thus, it is possible to form the catheter from a single filament or fiber which is wound in a two- or three-dimensional manner so that different filament sections of the single filament intersect or traverse one another, thereby allowing to manufacture a catheter with very low effort.

The filament structure may be free of cross-linked filament portions.

Alternatively, the filament structure may comprise a plurality of filaments being cross-linked to one another. Such a multiple filament architecture may allow to interweave two or more different filaments to thereby generate more sophisticated filament geometries. For example, it is possible with such an embodiment to produce a catheter having stronger mechanical properties, since a catheter wall may be formed by two or more filament structures overlapping and overlying one another.

The filament structure may be adapted as a hollow cylindrical structure (such as a tubing) enclosing a lumen (i.e. a volume through which a fluid may be conducted). For example, the filament structure may form a tube, wherein a material/substance exchange between a fluid within the tube and a fluid outside the tube is enabled via the exchange surface. In such an embodiment, a tubular catheter may be provided which can be appropriate for perfusion applications. A perfusion fluid may be guided through the lumen and may interact with a body fluid surrounding the catheter, when the catheter is inserted into a human body. Through the exchange surface, a material exchange can take place, so that a physiological parameter (such as a peptide or a glucose concentration) in the body can be monitored by analyzing the perfusion fluid after interaction with the body fluid via the exchange surface.

In an alternative embodiment, the filament structure may be adapted as a planar separation wall. For example, such a planar separation wall may separate two media, wherein an exchange of specific substances between the two media is possible via the exchange surface wall. Hence, the filament structure may be adapted as a planar separation wall for separating media on opposing sides of the planar separation wall.

The filament structure may be adapted as a braiding of a plurality of braided filaments. The filament structure may be adapted as a braiding of a plurality of braided filaments arranged according to a diagonal pattern. For example, a braided tube may be formed with such multiple filaments. This allows to provide a wall constituted by, in specific sections, several (two or more) interwoven filaments, thereby ensuring sufficient stability. At the same time, the displaceability of the filaments relative to one another may also provide for sufficient mobility and therefore flexibility. Thus, the catheter may withstand forces exerted when the catheter is being inserted into a body and at the same time may safely prevent further micro-injuries of the tissue since it may adjust its geometry to the anatomy of the body and reduce friction during insertion.

Still referring to the previously described embodiment, at least a part of the plurality of braided filaments may be aligned in a non-parallel manner relative to one another. For instance, it is possible that the intersection angle between the braided filaments is around 90°, typically between 80° and 20°. In such a manner, a stable braiding may be formed which at the same time allows a diffusion through holes between filament portions of the braiding.

The filament structure may also be adapted as a helically coiled single filament. In such an embodiment, it may be sufficient to use a single filament and form a helix from it by winding it in a cylindrical way. Adjacent windings of the helix may, in a force-free state, abut against one another, so that only very small interspaces or gaps may be formed between such helical structures, for instance when being bent or slightly elongated. Such an embodiment allows a very simple construction and at the same time an efficient exchange of substances through gaps between two essentially parallel aligned helical windings. Such an embodiment has also the advantage of a very high flexibility, since the entire wall of the filament structure is formed by one filament only, i.e. there is no portion at which two or more filament structures are sandwiched over one another.

In still another embodiment, the filament structure may be adapted as a helical structure formed by a plurality of coiled filaments. For example, the plurality of coiled filaments may be aligned in parallel relative to one another. Thus, in such an embodiment, two or more helices may be interwoven with one another, for instance may be arranged concentrically with different radii. In such an embodiment, the wall of the filament structure may be formed by two or more filaments. In another embodiment, the radii of the plurality of coiled filaments may be identical and they may be arranged in a concentric manner, however with a displacement of for instance one (or a multiple integer of one) filament diameters in the longitudinal direction. Such a configuration can be compared with two coil springs which are displayed relative to one another so that the windings of the different coil springs are arranged parallel to one another. A catheter of such an embodiment may have a larger rigidity as compared to a single filament helical structure, and may involve additional design parameters for adjusting the material exchange properties of the catheter.

In a coil configuration, the gaps may be oblong slits formed between adjacent windings. More precisely, the geometry of such a gap may be a helical structure as well.

In contrast to this, in a braiding geometry, the gaps may be small spots defined by several filament portions delimiting the dot.

In still in another embodiment, the filament structure may be adapted as a mesh formed by a plurality of first filaments and a plurality of second filaments angled relative to one another, for instance arranged with an intersection angle of basically 90°, particularly in the range between 80° and 100°. The intersection angle between the plurality of first filaments and the plurality of second filaments may be 90°. Such a configuration uses a web which may be formed by chaining threads or warp threads arranged along a first dimension and filling threads or filling yarns aligned along a second direction which may be essentially perpendicular to the first direction. The filling thread passes alternatively over and under the individual chaining threads.

The filament structure may comprise at least one of the group consisting of a metal, a plastic, a polymer, a glass fiber, a carbon fiber, and a natural fiber material. For instance, the filament structure may comprise a metal material, a plastic material, a glass fiber, or a carbon fiber. A metallic filament or wire (for instance made of stainless steel) has the advantage that it can be bent to form a rigid structure but maintains some flexibility to have channels via which substances can be exchanged. A metallic filament structure may on the other hand remain in place and shape without the exertion of external forces. A plastic filament may be made of Teflon, polytetrafluoroethylene, fluorinated ethylene propylene, polyurethane, polypropylene, polyethylene, polyamide, polyvinylchloride, a biocompatible polymer, or a biocompatible plastics.

In an embodiment, the filament structure may comprise an electrically conductive material (such as a metal) configured such that an electric signal is applyable to the filament structure to simultaneously function as an electrode. In addition to the substance exchange function, such a metallic filament structure may also be electrically coupled to an electrical signal source via which an electric signal (such as a constant or a time varying electric voltage) may be applied to the filament structure. Thus, it may be possible to generate an electric field by the filament structure, potentially influencing the exchange of loaded molecules.

In an embodiment, the catheter may comprise a fitting element (for instance a metallic one) via which the catheter can be connected to further components such as a fluid container, an analysis device, a pump, etc. Additionally, the filament structure may comprise a metallic material connected to the metallic fitting element for instance by soldering or any other metal-metal connection technique. Thus, the filament structure serving for substance exchange and/or as an electrode may also be used for a safe, reliable and simple connection to adjacent or neighboring metallic components.

The catheter may comprise an impermeable coating (for instance a tubular dielectric) covering a first portion of the filament structure, wherein a second portion of the filament structure may be free of the impermeable coating. Such an impermeable coating may be made of a material which does not allow exchange of substances (such as fluidic and/or solid components) over the impermeable coating. When such a coating covers a portion of the filament structure, this portion of the filament structure will not contribute to the substance exchange. By taking this measure, it is possible to spatially define with very simple measures and in an accurate manner in which portions of the catheter a substance exchange may take place and in which not.

Furthermore, the impermeable coating may protect the catheter in an efficient manner, since the portions of the filament structures which are covered with the impermeable coating may be configured specifically smooth to safely prevent injuries of a physiological object in which the catheter is inserted. For instance, the impermeable coating may be a polytetrafluoroethylene (Teflon) coating.

Still referring to the above embodiment, the filament structure may have a tubular shape having an inner surface and an outer surface, the impermeable coating covering a part of the inner surface. In such an embodiment, an inner impermeable coating, for instance a thin plastic tube, may be used as a support for manufacturing the filament structure, for instance by winding or weaving one or a plurality of filaments over this structure. After having finished this manufacture of the filament structure, it is possible to remove a portion of the supporting impermeable coating tube, thereby exposing portions of the filament structure to the lumen defined in an inner of the impermeable coating tube.

In an alternative embodiment (which however can be combined with the above embodiment), the filament structure may have a tubular shape having an inner surface and an outer surface, wherein the impermeable coating covers a part of the outer surface. In this embodiment, it is possible to deposit the impermeable coating onto the previously formed filament structure and to selectively remove portions of the impermeable coating to define exposed regions. This embodiment has the advantage that the smooth impermeable coating defines an outer surface of the catheter, and can therefore be smoothed to prevent damages of the medium in which the catheter is inserted.

A surface of the coating and/or of the filaments may be functionalized. This may include a surface activation, surface deposition, adaptation of mechanical properties, adaptation of chemical properties (for instance labeling with amino acids, free radicals, etc.), adaptation for surface charge (i.e. enabling to provide a positive, negative or neutral surface charge property) for the purpose of improving the quality and the performance of the catheter (such as a perfusion catheter). For example, such a functionalization may suppress occlusion of substance exchange holes, may suppress bacterial growth or may avoid substance adhesion. Such a functionalization may as well reduce risks associated with the use of such probes in living organisms, like coagulation, inflammation and rejection reactions. In an embodiment, the functionalization may include a heparinization.

In an embodiment, the filament structure may be arranged in such a manner that a multi-dimensional (for instance two- or three-dimensional) exchange surface is formed exclusively by friction between different portions of the filament structure. For example, a tubular arrangement formed of filaments may be held in this configuration simply by friction between different portions of contacting filament portions (and stabilizing coating at both sides). Therefore, no additional measures have to be taken for connecting the individual filaments to one another.

In an alternative embodiment, the filament structure may be arranged in such a manner that a multi-dimensional exchange surface is formed by connection elements connecting different portions of the filament structure. Such an embodiment may be particularly appropriate when a high rigidity of the catheter is desired. Then, small bridges or webs or bars or simply a dot of glue may be formed between contacting portions of the filaments. This may ensure a high rigidity and may safely prevent extensive movement of the filament structures relative to one another, also allowing to define with high accuracy a dimension of the gaps between the filament components or enclosed by the filament components.

The catheter may comprise at least one further exchange surface having a further filament structure or arranged to form a multi-lumen arrangement in combination with the filament structure. For example, two or more tubular exchange surfaces may be arranged concentrically to one another having holes or not, so that even complex fluidic paths can be realized by such a multi-lumen catheter.

The filament structure may be mechanically flexible. In this context, the term "flexible" may particularly denote a material property of the tube, namely that the tube can be reversibly deformed under the influence of an external force. More precisely, it can be reversibly deformed under the influence of external forces having an amplitude which force amplitudes are usually exerted when inserting a catheter into tissue of a human being with the muscle force of a surgeon.

The material of the filaments may be made of a shape memory material. With a shape memory material, the tube may be permanently held in a first state and, only when the temperature is raised above a threshold value, the material goes back to its original shape, for instance cylindrical shape. The required temperature may be supplied by the body temperature of a human being so that the tube may take its original shape automatically when being inserted into a living organism. Thus, by using a shape memory material for the filaments, the catheter may be inserted into the body in a "compressed" state, and can expand to its normal state under the influence of the body temperature.

In another embodiment, the catheter may be configured such that the exchange surface has a tubular shape having a longitudinal axis, wherein filament portions of the filament structure are arranged to include an angle with the longitudinal axis (different from zero), particularly an acute angle, for instance an angle of about 45°. In such a configuration, the longitudinal axis of the catheter does not correspond to an alignment direction of filaments.

The catheter may be adapted as a microperfusion catheter. In other words, substances may be exchanged via the gaps between different filament portions of a for instance tubular wall of the exchange surface in a similar manner as in the field of microperfusion.

The filament structure may be made of a biocompatible material. This may allow to use the catheter for surgical applications in living human beings or animals. In vitro applications are possible as well, for instance for analyzing cell cultures or testing adsorption properties.

Optionally, the catheter may comprise a delivery unit for delivery (or supply) of perfusion fluid to (for instance a lumen of) the structure in a manner to allow for an exchange (mono-directionally or bidirectionally) of substances between a surrounding medium (such as tissue of a physiological subject) and the perfusion fluid (that is from the tissue to the perfusion fluid, and/or in the opposite direction) via the filament net.

The delivery unit may comprise a perfusion fluid container containing the perfusion fluid and being in fluid communication with the (for instance lumen of) the structure. Such a perfusion fluid container may be a reservoir holding the perfusion fluid. The perfusion fluid container may contain a medication, particularly insulin. The insulin supply to the organism may be made dependent on the glucose concentration in the organism. The perfusion fluid may be used for both detecting the glucose concentration in the surrounding blood and for supplying a proper dose of insulin to control the glucose concentration to a desired value.

The drain unit may comprise a perfusion fluid collector collecting the perfusion fluid after the exchange of substances between the tissue and the perfusion fluid via the holes between the filament structure. Such a collector may be a waste container or may be a member in or from which the perfusion fluid is analyzed after exchange with the body fluid. Such an analysis may include the measurement of a concentration of a substance.

The delivery unit and/or the drain unit may comprise a perfusion fluid transport unit, particularly a pump, for instance a peristaltic pump, for transporting the perfusion fluid through the lumen of the structure. Transport of the fluid may be carried out by pumping, sucking, etc. The catheter may be operated, for example, in a push mode, in a pull mode, or in a push-pull mode.

The drain unit may comprise an analysis unit adapted for analyzing the perfusion fluid after the exchange of substances between the tissue and the perfusion fluid via the filament structure to thereby derive information regarding the tissue or, more generally, regarding the physiological subject. Such an analysis may include the determination of the presence or absence of a substance, the determination of the concentration of a substance, and/or a calibration.

The delivery unit may be connected to a first end portion of the exchange surface or catheter, and the drain unit is connected to a second end portion of the exchange surface or catheter. Thus, the transport of the perfusion fluid may be effected in a first direction, whereas the exchange between the perfusion fluid and the surrounding organism may be effected in a second direction which may be essentially perpendicular to the first direction.

Next, further exemplary embodiments of the method of manufacturing a catheter will be explained. However, these embodiments also apply to the catheter, to the method of operating a catheter and to the method of use.

The method may further comprise removing (for instance exclusively a sub-portion of) an impermeable coating (such as a tubing) covering the filament structure to thereby expose a portion of the filament structure from the impermeable coating. Such a coating may be deposited on the filament structure, and/or the filament structure may be wound on a coating. Subsequently, specific portions of the coating may be removed, for instance by lithography and etching procedures, so as to define a patterned surface via which a substance exchange is enabled, and to define portions in which the impermeable coating maintains on the filament structure so that these portions do not allow for an exchange of substances.

According to a preferred embodiment, the impermeable coating may be removed by a laser treatment. Such a procedure is a very simple and precise way of defining such a patterned surface and can be realized by directing a laser beam only onto selected surface portions of the impermeable coating which are to be removed.

The manufacturing method may further comprise forming the exchange surface by winding one or more filaments in a two-dimensional or three-dimensional manner to thereby form the filament structure. Thus, the starting point of the catheter manufacture may be one or more oblong filaments which may be bent to form a network of overlapping, traversing and/or cross-linked filament portions between which small spaces remain serving as the filter holes.

In the following, further exemplary embodiments of the method of operating a catheter will be explained. However, these embodiments also apply to the catheter, to the method of manufacturing a catheter and to the method of use.

The method may comprise inserting the catheter into a physiological object.

The filament structure may be mechanically flexible and may be stretched during inserting the catheter into the physiological object to thereby reduce a cross-sectional area of the catheter during inserting. Conventionally, it may be a bottleneck of catheter technology to insert a catheter into a human body such as a blood vessel or a tissue like brain tissue or skin tissue. Therefore, during the insertion procedure, a longitudinal stretching or pulling at the catheter according to an exemplary embodiment may allow the filament portions to be slightly displaced relative to one another so that the catheter is longitudinally expanded and consequently radially compressed since the entire length of the filaments remains constant. When the catheter is inserted into a tissue or small dimensioned body opening, the stretching procedure may be finished so that the catheter radially expands and is longitudinally relaxed to the normal or equilibrium length. This advantageous property can be obtained as a result of the filament architecture, since this allows a high degree of flexibility.

Next, further exemplary embodiments of the method of use will be explained. However, these embodiments also apply to the catheter, to the method of manufacturing a catheter, and to the method of operating a catheter.

The method may comprise using the catheter for measuring a concentration of at least one of the group consisting of a physiologically active substance in a physiological object, a physiologically inert substance in the physiological object, and a sample analyzed in vitro. The catheter may be used for measuring a concentration of a physiologically active substance in a physiological object. By measuring the concentration of a physiologically active substance at a specific position within the body of the human being, the impact of an external influence, for instance contacting the body with a product like a cosmetics or a medication, can be investigated.

The method may comprise using the catheter for measuring an effect of a physiologically active substance, particularly in a physiological object. The method may further comprise using the catheter for measuring an effect of a physiologically effective intervention or physiologically active substance in a physiological object. Thus, not only the physiologically active substance itself (for instance insulin) may be measured, but also the impact thereof.

The method may comprise using the catheter for determining a concentration of a physiologically active substance, particularly in a physiological object. Furthermore, according to the method, the catheter may be used for determining an advantageous or desired concentration of a physiologically active substance in a physiological object. In other words, the catheter may be used in the context of developing a new medication by optimizing a concentration or dose of the medication to obtain a certain impact.

The catheter may further be used for determining a physiological parameter in a physiological object, particularly in basic research.

The method may comprise using the catheter for the delivery of a physiologically active substance, particularly to the physiological object.

The method may comprise using the catheter for a simultaneous or subsequent determination of one or more physiological parameters released or modulated due to the delivery of the physiologically active substance.

According to an exemplary embodiment, a tube may be provided in which a lattice or mesh is inserted or which consists of the lattice or mesh. Such a filament-based tube may be any kind of web or helical structure with close by located helices. Also parallel wire loops may be used for forming such a filament-based structure.

Such embodiments may allow to obtain proper exchange characteristics with a simultaneously small dimension. The surface structure may be reduced or minimized so as to obtain a high exchange surface. Such embodiments are simple in manufacture and may have advantages for forming interfaces to a tubing being appropriate for being implanted in an object such as a living organism. The filament structure may also serve as a mechanical support structure being sufficiently flexible. A double wall configuration of permeable and impermeable material (with the impermeable material being removed from a portion of the permeable material) may allow for spatially well definable filter characteristics without a deterioration of the stability. Moreover, an advantageous ratio between exchange surface and supporting surface may be obtained allowing for an increase or a maximization of exchange effectiveness by an increase or a maximization of the portion of surrounding tissue involved in substance exchange with the perfusion fluid.

Such embodiments may involve a very small amount of material resulting in a light-weight arrangement and at the same time may allow to obtain a proper stability and a high and effective exchange surface.

According to an exemplary embodiment, a mesh-like, braid or coil-like perfusion catheter may be provided. Such a catheter may be provided with a micromesh to obtain a high exchange area. Such a micromesh or grid may allow to serve as an exchange surface.

According to an exemplary embodiment, a system for providing a catheter is provided for insertion into biological tissue for continuous sampling of interstitial fluid (or other body fluids) and substances included therein for subsequent analysis of at least one physiological parameter. By taking this measure, the exchange characteristic may be improved or optimized and an improved flexibility for designing the exchange surfaces may be obtained.

In accordance with these boundary conditions, an exemplary embodiment of the invention provides a plastic tube reinforced with a braid which can be coated on an inner and/or outer surface (for instance with Teflon), wherein such a semi-finished product may be processed (for example by a laser) so that in defined portions the coating may be removed so that only the braid—as tissue supporting element and exchange portion with the tissue—may be maintained.

Such embodiments may be realized, for example, in a linear shape or with concentric geometries.

An architecture of the filament winding can be an ordered structure having a symmetry or may be completely random. Transversely arranged/slanted filament sections may be provided to intentionally disturb a low-friction longitudinal streaming, therefore disturbing laminar streaming conditions and involving turbulence. The efficiency of the exchange in an edge zone may therefore be improved, without depending exclusively on diffusion, since an influence of a dead volume may be reduced.

Due to the automatic manufacturability of the catheter, a high reproducibility may be guaranteed. The exchange portions may be manufactured in any desired shape and in very small geometric dimensions. Using imaging methods (micro computed tomography (CT), ultrasonic waves, etc.), it is possible to make the catheter visible and localizable within the physiological object. The freely designable surface of the catheter may involve advantages for preventing the adsorption of adsorptive substances. Between the exchange surfaces, it is possible to intentionally form non-exchange surfaces.

In an elongated state, the outer dimension of the catheter in a central section may be at a minimum, so that perfusion fluid may be forced to accumulate at the surface. Simultaneously, the channel may be reinforced by the increasing small meshed properties. The varying size of the exchange holes may provide safety against undesired occlusion. The catheter may have a self-supporting feature in case of a large elongation. When inserting the catheter in a body duct or in a surgically created duct, the structure may be longitudinally expanded, therefore the fibers may be aligned towards a longitudinal direction of the lattice, resulting in a reduction of the diameter and a reduction of the width of the meshes. This may reduce the frictional resistance, may prevent the tissue from damage, and may be a prophylaxis against an undesired occlusion.

A catheter for detecting parameters of biological systems (for instance in interstitial fluid of living organisms) may be produced on the basis of a braided cubing. A coating of the sealed tube can be selectively removed at defined positions (exchange areas) so that only the braid remains exposed to the surrounding medium. The permeable structure of the braid may serve for a communication (of fluids, liquids, substances, particles, cells, pressure, optical properties, etc.) between an inner side (perfusate side) and an outer side (tissue side) of the tubular catheter.

The exposed portion, i.e. the exposed braid, may serve as an ideal exchange surface towards the tissue regarding the tissue supporting effect and the available surface for exchange procedures, without deteriorating the mechanical robustness of the tube structure. Such an embodiment can be formed in an automatic manner to meet even high hygienic standards, and may allow for a cost-efficient manufacture in large numbers.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

FIG. 1 schematically illustrates a catheter according to an exemplary embodiment of the invention.

FIG. 4 to FIG. 6 illustrate different geometries of a filament structure of catheters according to exemplary embodiments of the invention.

The illustration in the drawing is schematically. In different drawings, similar or identical elements are provided with the same reference signs.

Figure 1:
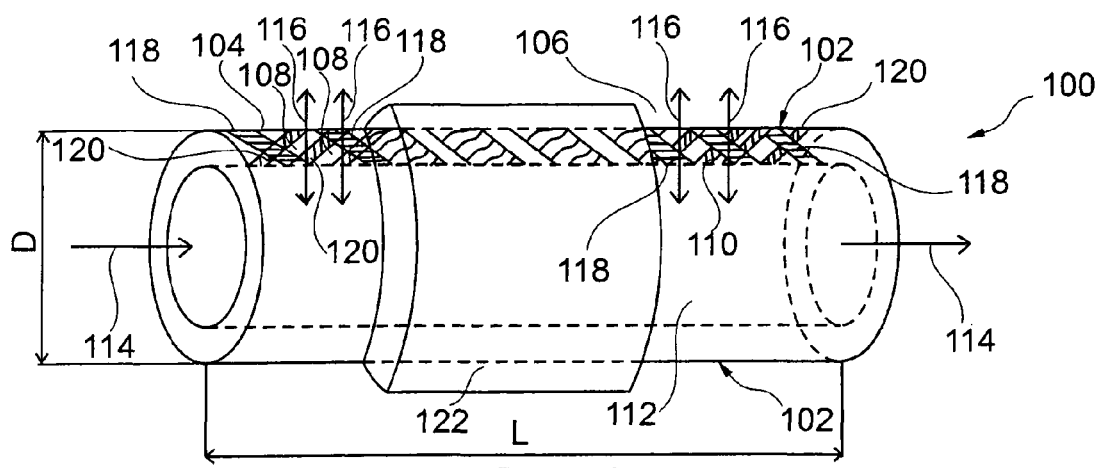

In the following, referring to FIG. 1, a membrane-free perfusion catheter 100 for accessing fluid/tissue according to an exemplary embodiment of the invention will be explained.

The catheter 100 comprises a membrane-free permeable exchange surface (or wall) 102 which is shown schematically in FIG. 1 and which will be described below in more detail. The permeable exchange surface 102 is shaped as a hollow tube. An outer surface 104 of the hollow tube 102 is brought in direct contact with the sampling fluid 106 (such as interstitial fluid) in an object of investigation (such as a human being). Substances of the sampling fluid 106 are capable of traversing the permeable exchange surface 102 through gaps 108 of defined size and diameter in the permeable exchange surface 102 during a microperfusion procedure.

The permeable exchange surface 102 has a second, inner surface 110 adapted to be brought in contact with a perfusion fluid indicated schematically with reference numeral 112. The perfusion fluid 112 may be pumped through the hollow channel enclosed by the permeable tubular exchange surface 102 (in a pumping direction indicated by arrows 114), and can be selectively brought in interaction with components of the sampling fluid 106 diffusing or migrating through the permeable exchange surface 102, as indicated schematically by double arrows 116. The catheter 100 is adapted to be implanted in a tissue (or artery or vein) of a patient and may stay there for, for instance, 72 hours. By the substance equalization via the exchange surface 102, concentrations of components of the sampling fluid 106, for instance a glucose level, can be monitored by analyzing the perfusate 112 with a corresponding sensor in fluid communication with the perfusate 112.

As indicated schematically in FIG. 1, the permeable exchange surface 102 is constituted by first filaments 118 and by second filaments 120, which are interwoven with one another in a diagonally overlapping manner to form a mesh structure. The ordered arrangement of the first filaments 118 and the second filaments 120 relative to one another results in a deterministic ordered arrangement of the gaps 108. The latter have a defined size (in contrast to a merely statistical distribution of arbitrary sizes) which may be, for instance, 1 µm and therefore larger enough to allow basically all molecules and macromolecules in the sampling fluid 106 to pass the permeable exchange surface 102. The material of the filaments 118, 120 may be impermeable (however may be, in other embodiments, permeable as well), but as a result of the mesh architecture, the gaps 108 are formed between different portions of the filaments 118, 120 so that an exchange of substances having a dimension smaller than a dimension of the gaps 108 is enabled. The cylindrically wound and interwoven filaments 118, 120 together enclose a lumen through which the perfusion fluid 112 is pumped or passively flowing. The filaments 118, 120 may be made of a plastic material.

As can be taken from FIG. 1, over a central portion of the permeable exchange surface 102, a tubular Teflon coating 122 is formed which is impermeable for fluids. This Teflon coating 122 may be formed on the mesh 118, 120 and may be subsequently patterned by laser processing so that only the central portion of the catheter 100 remains covered with the impermeable layer 122. By maintaining the impermeable layer 122 only on the central portion of the catheter 100, substance exchange 116 is only enabled on the left-hand side and on the right-hand side of the central portion in which the layer 122 is located. An outer surface of the impermeable layer 122 is smooth so as to allow the catheter 100 to be inserted into living tissue of a human being without the danger of injuring tissue more than indented.

The filaments 118, 120 are interwoven in such a manner that only friction maintains the structure 102 in position. Thus, the catheter 100 has highly flexible mechanical properties, wherein upon, for instance, pulling longitudinally at the filaments 118, 120, a diameter D can be temporarily reduced, whereas a length L may be temporarily increased. This may simplify insertion of the catheter 100 into a body.

In the following, referring to FIG. 2, a catheter 200 for sampling fluids and cells in living tissue according to another exemplary embodiment will be explained.

The catheter 200 comprises a braided polyimide tubing being

Teflon coated on the inside. The outside of the catheter 200 may be coated by an impermeable polyimide Teflon composite layer 204. Selectively in sections 206, tubing 204 is removed from braiding 202 to expose the braiding 202 for fluid exchange. A marker band is denoted with the reference numeral 208. The outer diameter of the polyimide Teflon composite layer 204 is 0.4 mm, and the inner diameter is 0.25 mm. The braid 202 consists of eight wires. The flat wire used has a width of 0.0635 mm and a thickness of 0.0127 mm. The embodiment of FIG. 2 is configured as a catheter for intracerebral (Hippocampus) measurements. The catheter 200 is laser processed which is performed to form two separate exchange areas 206.

Figure 2:
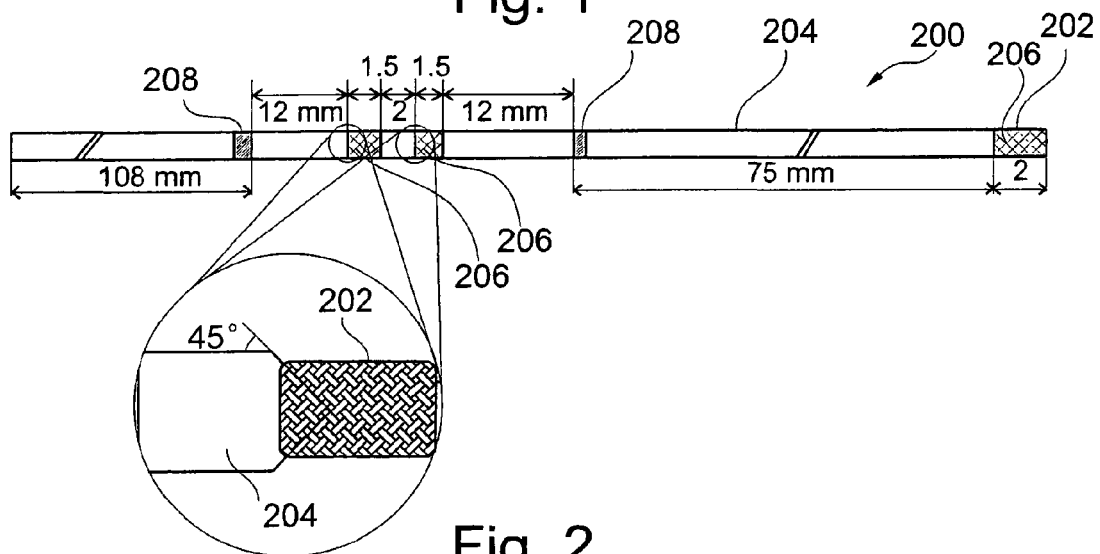
FIG. 2 and FIG. 3 illustrate catheters according to other exemplary embodiments of the invention.
Figure 3:
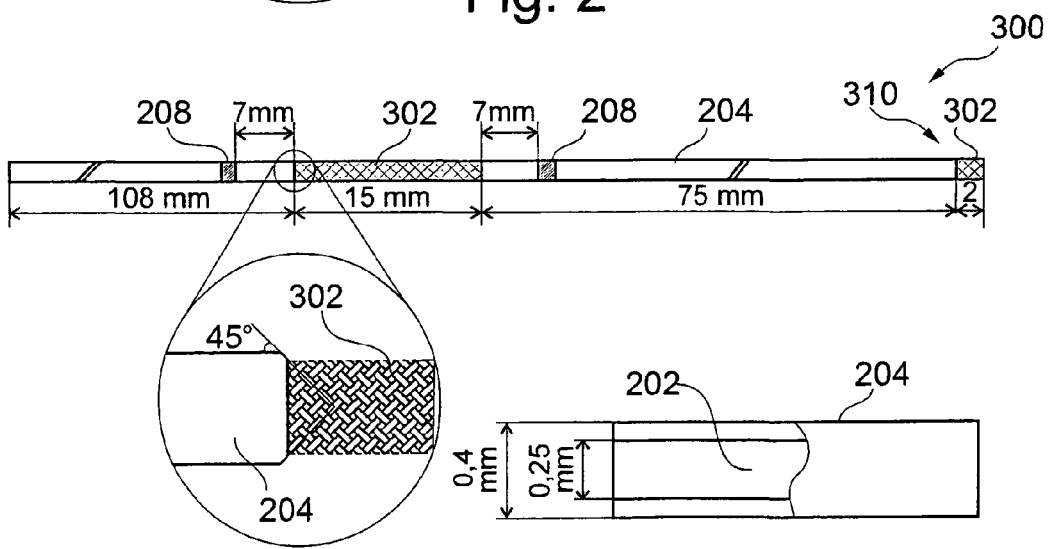

FIG. 3 shows a catheter 300 according to another exemplary embodiment of the invention which is very similar to the catheter shown in FIG. 2 but is adapted for intradermal measurement.

The portions at which the coating 204 is removed are denoted with reference numeral 302. The catheter 300 for intradermal use comprises a braided tubing having two marker bands 208 which are embedded in the tubing visible from the outside to center the exchange area during implantation. In the exchange areas 302, the polymer layer 204 is removed and the stainless steel braid 202 is exposed, so that fluid and cells are able to pass over from inside to outside, and vice versa. On a tip 310 of the tubing, the braid 302 is exposed to be able to connect an implantation needle.

The edge on the backside of the exchange area 302 may optionally be 45° sloped to minimize implantation trauma. The tubing outside 204 of Teflon polyimide composite is provided to reduce friction during the implantation process to provide chemical inertness.

FIG. 4 shows a filament structure 400 formed by a first filament 402 which is wound in a helical manner concentrically with a second filament 404 which is also wound in a helical manner parallel to the filament 402 so that a double helix structure is obtained. In areas 406 in which adjacent windings of the helices 402, 404 abut to one another, a small gap (not shown) may be formed which allows substance exchange.

FIG. 5 shows a filament structure 500 according to another exemplary embodiment, serving as an exchange surface. The helix 500 is only shown schematically and will, in practice, have a thicker filament 502 and smaller gaps 504 between adjacent windings of the filament 502. Between adjacent windings 502, exchange between the lumen enclosed by the helix 502 and the surrounding medium is enabled. Thus, the helical coiling 500 is made of a single filament.

FIG. 6 illustrates a filament structure 600 according to another exemplary embodiment of the invention in which a matrix-like web is formed by first filaments 602 aligned along a first direction and second filaments 604 aligned along a second direction perpendicular to the first direction. The first filaments 602 may be denoted as chaining threads, whereas the second filaments 604 may be denoted as filling threads. The web 600 is formed by the wave-like arrangement of the filaments 602, 604 by which a web structure is formed enclosing gaps 606 through which a substance transfer may be carried out. Thus, the structure 600 may also serve as an exchange surface.

Figure 7:
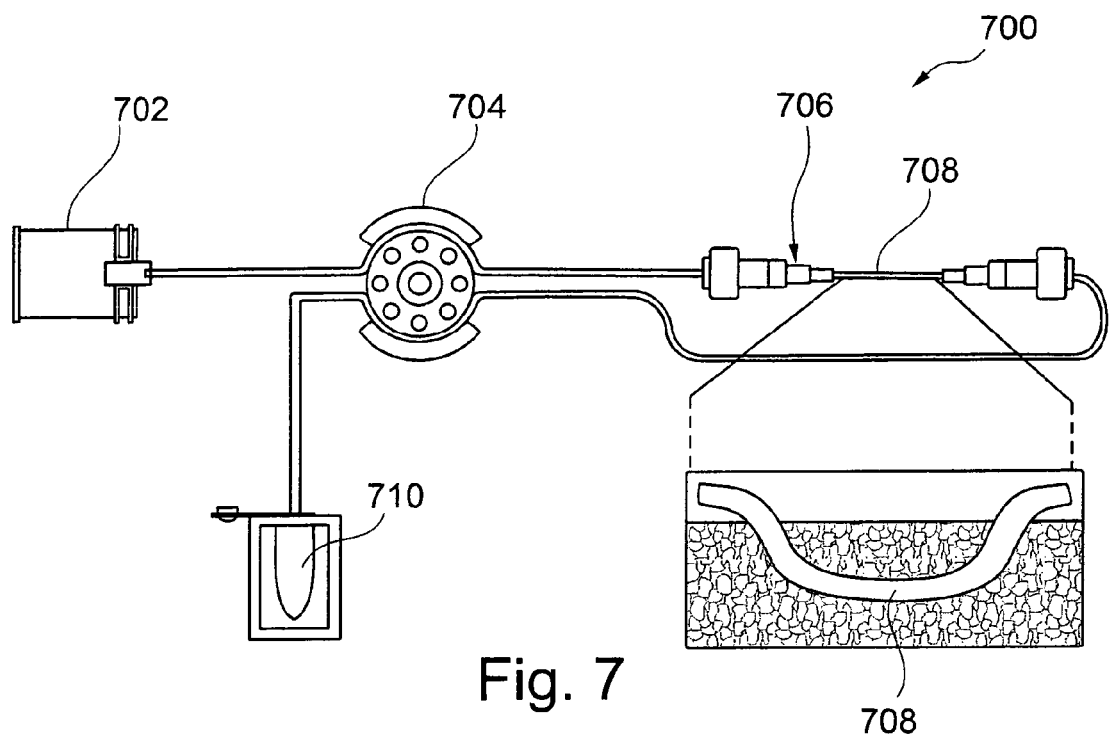
FIG. 7 illustrates an open flow microperfusion system according to an exemplary embodiment of the invention.

FIG. 7 illustrates a microperfusion system 700 according to an exemplary embodiment of the invention.

The microperfusion system 700 comprises a perfusate container 702 via which a perfusate fluid may be pumped by a syringe/peristaltic pump 704 through a catheter 706 having an exchange surface 708 with a filament structure, as described above referring to the previous figures. After the perfusate fluid has been pumped through the catheter 706, it may be pumped back through the peristaltic pump 704 and may be collected in a vial 710.

For pharmacological studies in medical research, measurement of substances in determined tissues provides important information. Methods like microperfusion allow access to these data. Especially for measurement of pharmacokinetic and pharmacodynamics parameters, microperfusion is valuable.

The catheter 708 is connected to an implantation system which is removed after implantation and the pump 704 is connected to provide flow to the inner lumen of the catheter 708. Over the exchange area, substances can pass from the outside of a catheter 708 (tissue) to the inside (perfusate) and vice versa. The perfusate is collected in the vial 710 after leaving the catheter 708. It is possible to calculate the concentration of a substance and tissue in a period of time. This allows acquiring pharmacokinetic/-dynamic parameters in that time dependence.

In the following, referring to FIG. 8, a catheter system 800 according to an exemplary embodiment of the invention will be explained.

Figure 8:
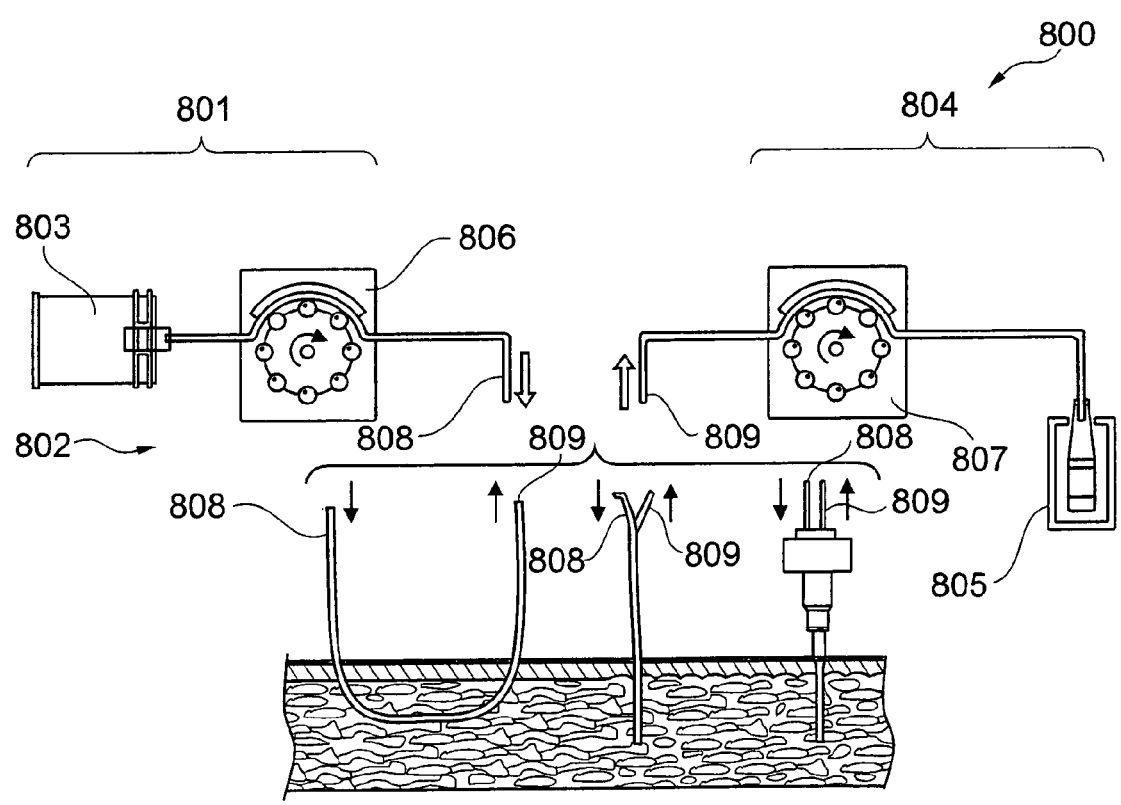
FIG. 8 shows a catheter system according to an exemplary embodiment of the invention.

The catheter system 800 comprises a delivery unit 801 for delivery of perfusion fluid to a lumen of a tubular catheter structure 802 in a manner to allow for an exchange of substances between the tissue and the perfusion fluid via a filament-based exchange surface forming the tubular catheter structure 802 (not shown in FIG. 8).

The delivery unit 801 comprises a perfusion fluid container 803 containing the perfusion fluid and being in fluid communication with the tubular catheter structure 802.

The catheter system 800 further comprises a drain unit 804 for draining the perfusion fluid after the exchange of substances between the tissue and the perfusion fluid via the holes in an interior of the filament network of the tubular catheter structure 802. The drain unit 804 comprises a perfusion fluid collector 805 collecting tissue fluid or the perfusion fluid after the exchange of substances between the tissue and the perfusion fluid via the tubular catheter structure 802.

The delivery unit 801 comprises a first pump 806 and the drain unit 804 comprise a second pump 807, both for transporting the perfusion fluid through the lumen of the tubular catheter structure 802.

The delivery unit 801 is connected to a first end portion 808 of the tubular catheter structure 802, and the drain unit 804 is connected to a second end portion 809 of the tubular catheter structure 802.

FIG. 8 is a schematic representation of a system 800 for the perfusion of tissue/an organism/a unit cell structure in connection with a catheter according to an exemplary embodiment of the invention. Three catheter designs 802 are shown exemplarily. Catheters 802 feature an exchange area towards the organism and two connections 808, 809 to a peripheral system 801, 804. System 801, 804 and catheter 802 allow the simultaneous inflow of a perfusion fluid, and outflow of the perfusion fluid after interchange with the organism across the catheter's exchange area. The schematics of FIG. 8 shows two pumps 806, 807, here exemplarily peristaltic pumps. In principle any kind of pump or mechanism can be utilized that leads to a flow of fluid through the system 800.

Figure 9:
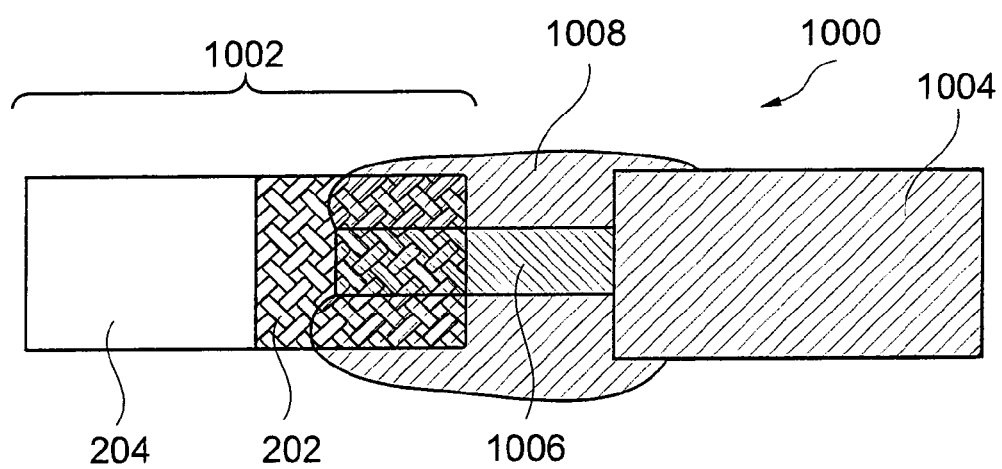
FIG. 9 shows a connection between a catheter and an insertion needle according to an exemplary embodiment of the invention.

FIG. 9 illustrates a connection structure 1000 between a catheter 1002 according to an exemplary embodiment of the invention and an implantation needle 1004 with a hole wire crimped.

The catheter 1002 is formed by a catheter tubing 204 and a braid 202. A connection between the catheter 1002 and the needle 1004 is performed via a solid wire 1006 which connects the lumen of the catheter 1002 with the implantation needle 1004 by a gluing connection provided by an UV cured adhesive 1008.

In the implantation needles 1004 backside, there is a hole in longitudinal direction. A solid wire 1006 is crimped in with minimal deformation of the needle 1004. On the tip of the catheter 1002, the polymer layer 204 is removed to get UV adhesive 1008 in contact with the metallic braid 202 for a robust connection. After curing with UV light, the connection is tough with a smooth surface.

In the following, referring to FIG. 10 to FIG. 16, a method of using a catheter according to an exemplary embodiment of the invention will be explained. The catheter used in FIG. 10 to FIG. 16 is a minimally invasive catheter of a linear type for application in cutaneous (skin) and subcutaneous fat tissue applications to be operated by medical users. For instance, catheter 1700 shown in FIG. 17 to FIG. 19 may be used.

The catheter allows for a smooth access to the target tissue and delivers liquid samples as a basis for an analysis of the biochemical conditions at the target tissue. For this purpose, a biocompatible or physiologically compatible liquid (perfusion fluid) can be guided with a very small flow rate (for instance in a range between 0.1 µl/minute and 10 µl/minute) through the catheter according to the principle of microperfusion. The perfusate can, thanks to its open membrane-free exchange surface, receive practically all substances from the surrounding medium to supply them for lab analysis in collected sample fractions. The catheter has to be inserted into the tissue under aseptic conditions.

Figure 10:
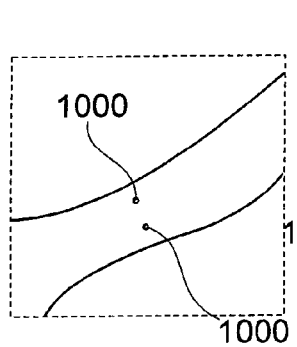
FIG. 10 to FIG. 16 show images illustrating implantation of a membrane-free perfusion catheter according to an exemplary embodiment in an arm of a patient.

As can be taken from FIG. 10, the skin of the patient should be disinfected at the application position. Positions close to which the catheter is to be inserted into the body and is to be guided out of the body are denoted with reference numeral 1000 and may have a distance from one another of about 3 cm.

Figure 11:
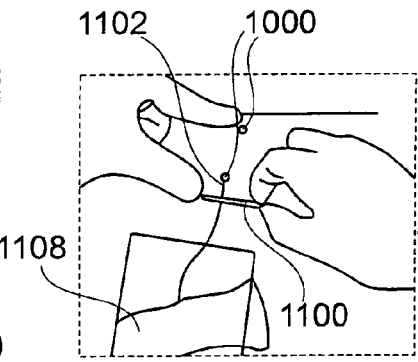

Now referring to FIG. 11, opened sterile inner packaging 1108 of the catheter should be placed in such a manner that its opening is directly located at the position 1000 of inserting the catheter. Using a sterile needle holder 1100, insertion needle 1102 can be arranged about 1 cm away from its end. A protection cover may be removed from the tip of the needle 1102. Then, the needle 1102 may be guided through the tissue until the needle 1102 comes out of the tissue again by 1 cm. The catheter tube itself preferably remains within the sterile package. Alternatively, the corresponding region can also be covered in a sterile manner. It should be prevented to pierce directly through the markings 1000, but the piercing should be slightly adjacent to the markings 1000. During insertion into the skin (dermis), the skin can be tightly stretched. During insertion into subcutaneous fat tissue, it is recommendable to form a slight skin fold with the other hand.

Figure 12:
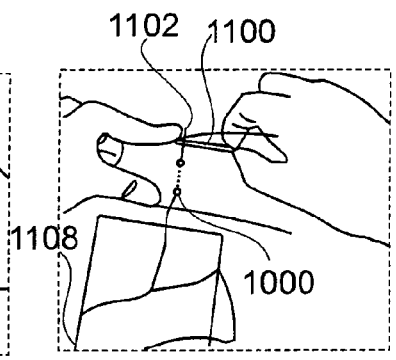

As can be taken from FIG. 12, a tip of the needle 1102 may be operated by the needle holder 1100, and the catheter is pulled with its exchange surface (region between the markings 1000) into the tissue. Pulling should be performed in such a way that insertion channel, catheter and needle always form a straight line. With the other hand, it is possible to maintain the tissue or the skin, respectively, tightly stretched.

Figure 13:
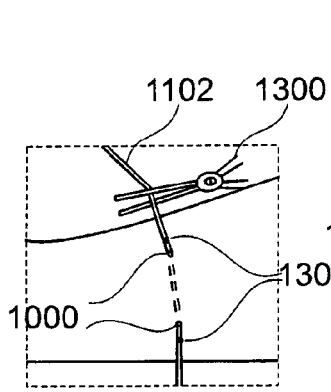

As can be taken from FIG. 13, the needle 1102 can then be removed using a sharp sterile scissor 1300, and then a supporting wire (in an interior) may be removed. Thus, sharp sterile scissor 1300 is used for cutting the catheter tube about 1 cm away from the needle, thereby removing the needle 1102. A cap may be removed from a first luer lock for sliding the support wire into the luer lock so that it is possible to pull out the wire at the other (cut) end. Catheter markings 1302 indicate and delimit a catheter portion to remain inserted within the body.

Figure 14:
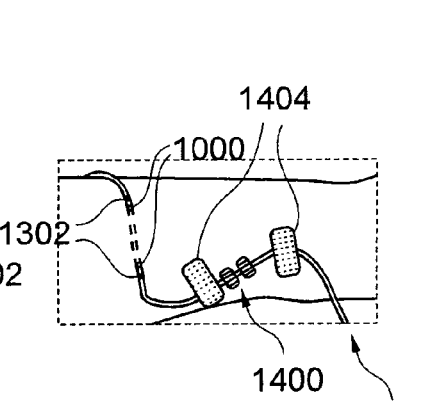

As can be taken from FIG. 14, the first luer lock may be connected with a tube to the perfusate container. The first luer lock is denoted with reference numeral 1400 in FIG. 14. The perfusate container may be connected to a position 1402. As can be taken from FIG. 14, the catheter may be adhered to the body in such a manner that undesired getting out of place of the catheter may be prevented. This may be accomplished by adhesive tapes 1404.

Figure 15:
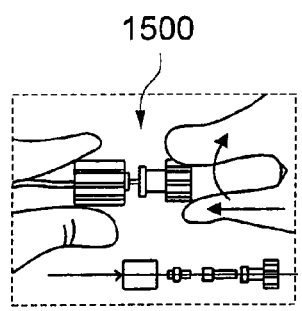

Optionally, as shown in FIG. 15, if an operation in a push or push-pull mode is desired, it is possible to tightly screw a second luer lock 1500 onto the cut end of the catheter. For this purpose, the catheter end may be slid centrally through the opening in the luer connector until the end is plane-parallel with the inner end. Subsequently, the connector may be fixed by screwing.

Figure 16:
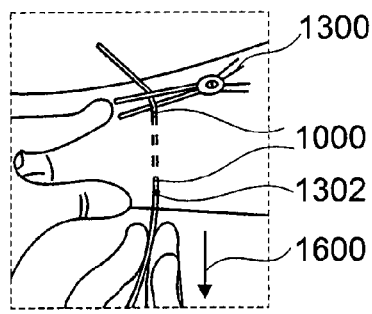

Now referring to FIG. 16, for removing the catheter, sterile scissor 1300 may be used for cutting the catheter close to one of the piercing positions. The catheter may be pulled out of the body in a longitudinal direction (see arrow 1600). In case of a resistance, it is possible to tightly stretch the skin.

Figure 17:
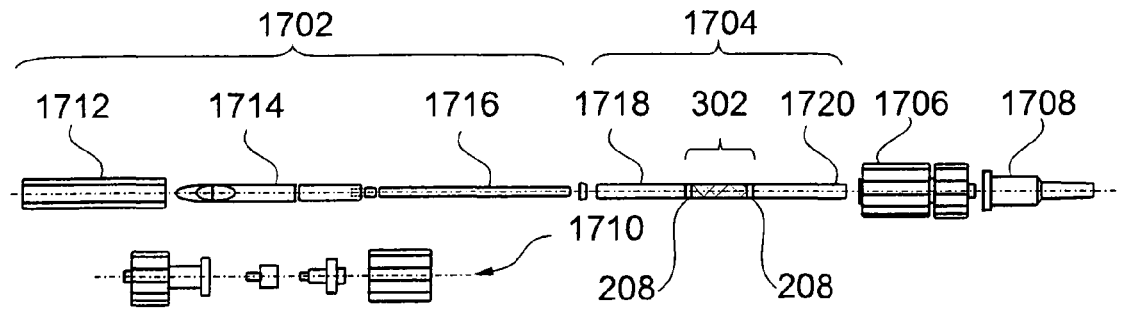
FIG. 17 illustrates an explosion view of a membrane-free perfusion catheter according to an exemplary embodiment of the invention.
Figure 18:
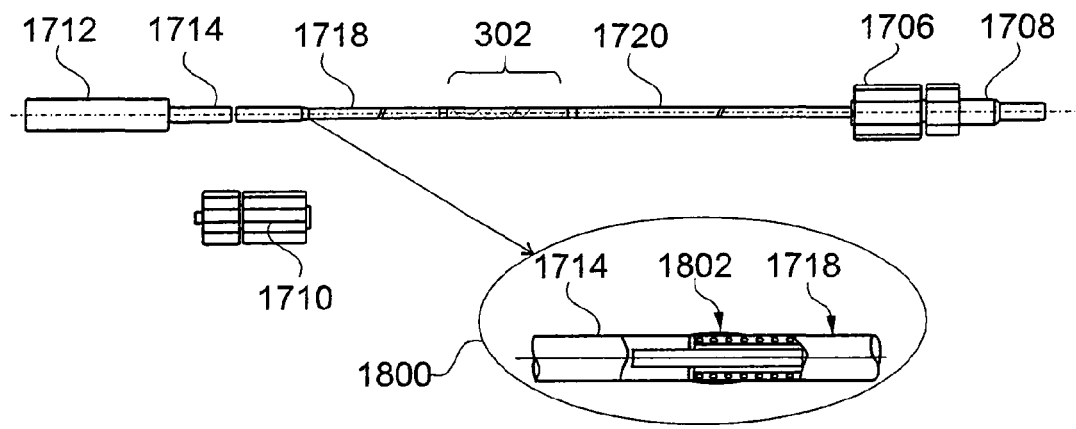
FIG. 18 illustrates an assembled configuration of the catheter of FIG. 17 in an operation state before insertion into a patient.
Figure 19:
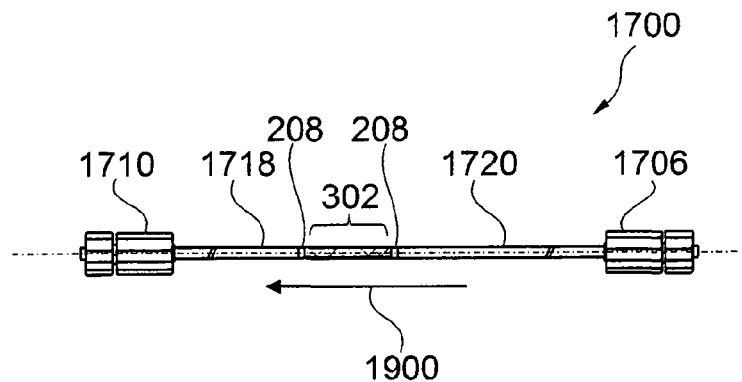
FIG. 19 shows the catheter of FIG. 17 and FIG. 18 in an operation state after insertion into the patient.

FIG. 17 to FIG. 19 show a membrane-free perfusion catheter 1700 according to an exemplary embodiment of the invention.

As shown in FIG. 17, the catheter 1700 comprises an insertion needle portion 1702, a catheter tube 1704 with a central membrane-free exchange surface 302, a first luer lock connector 1706, a cap 1708 and optionally a second luer lock connector 1710. The insertion needle 1702 comprises a cap 1712, a metallic needle portion 1714 and a support wire 1716. The catheter tube 1704 can be realized as a polyimide tube, being covered internally and externally with Teflon (Polytetrafluoroethylene) and having a stainless steel insert. Impermeable side sections 1718, 1720 are separated by a permeable exchange surface 302 having a filament structure forming the actual membrane-free perfusion section. Markings 208 delimiting the membrane-free perfusion section 302 are shown as well. Catheter tube 1704 may have a length of 203 mm, an inner diameter of 0.25 mm, an outer diameter of 0.325 mm, and a flow rate in a range between 0.1 µl and 10 µl/min.

The luer lock connectors 1706, 1710 may be made of polycarbonate.

FIG. 18 shows the catheter 1700 in an operation state prior to insertion into the human body with the cap 1712 attached to the needle 1714. Furthermore, FIG. 18 shows a detail 1800 illustrating how an interface section between metal needle 1714 and portion 1718 of the tubular catheter section 1704 can be configured. An adhesive 1802 connects the needle 1714 to the catheter tube 1718.

FIG. 19 shows the catheter 1700 in an operation state after insertion. An arrow 1900 illustrates both an insertion direction and a perfusate flow direction.

Figure 20:
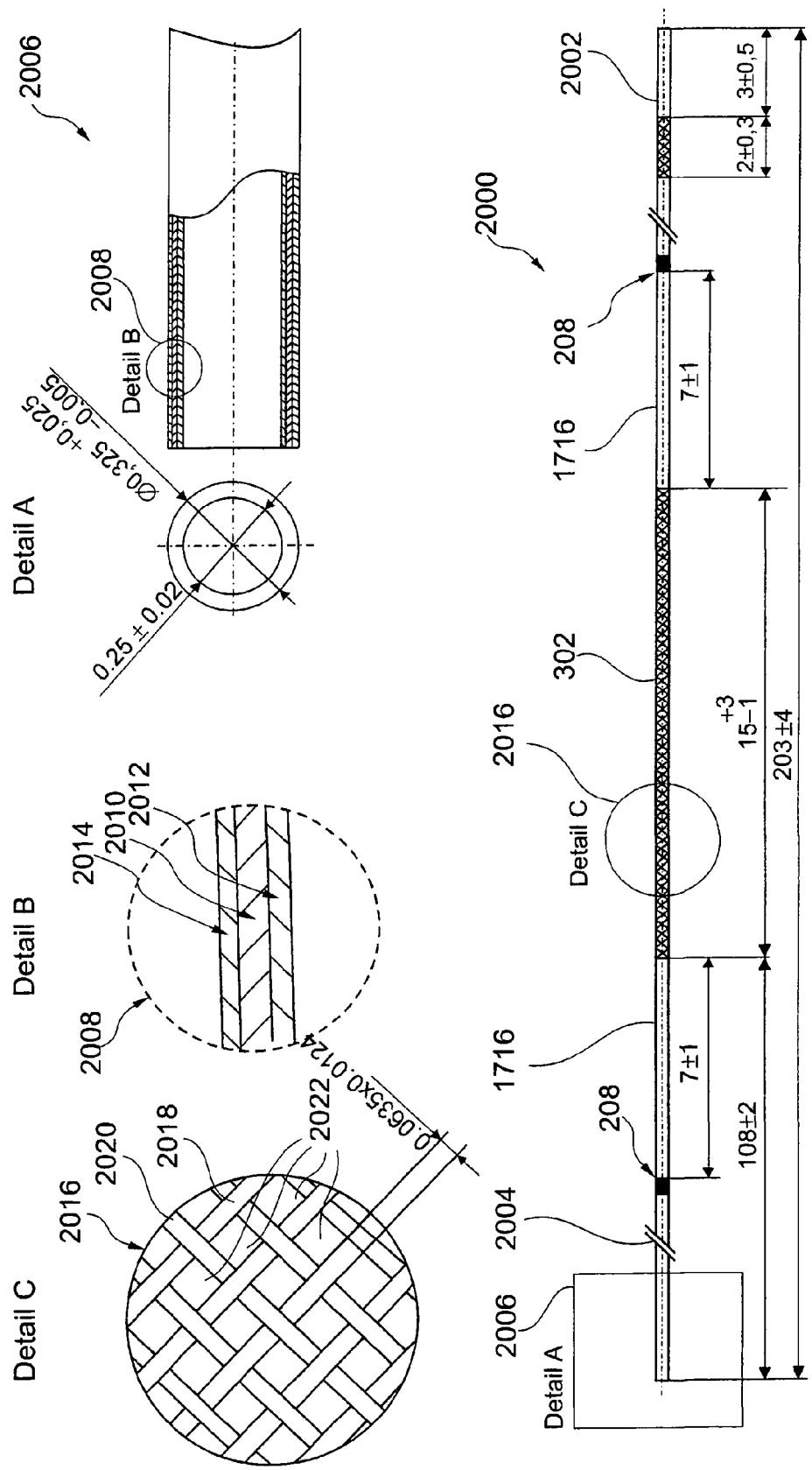
FIG. 20 shows a membrane-free perfusion catheter according to an exemplary embodiment of the invention together with a number of detailed views.

FIG. 20 shows an enlarged view 2000 of catheter section 1704. An inlet side is denoted with reference numeral 2002, whereas an outlet side is denoted with reference numeral 2004. Detail A, see reference numeral 2006 shows a constitution, in a cross-sectional illustration, of an outlet section of the catheter. As can be taken from detail B (being, in turn, a detail of detail A), see reference numeral 2008, this portion of the catheter comprises a braid/polyimide 2010 sandwiched between an inner Teflon tube 2012 and an outer Teflon tube 2014.

A detail C, see reference numeral 2016, illustrates the wound filaments 2018, 2020 forming the membrane-free exchange surface with a defined dimension of recesses 2022. Selectively in section 302, braid/polyimide 2010 is exposed by locally removing inner Teflon tube 2012 and outer Teflon tube 2014.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

Implementation of the invention is not limited to the preferred embodiments shown in the figures and described above. Instead, a multiplicity of variants are possible which use the solutions shown and the principle according to the invention even in the case of fundamentally different embodiments.

The invention claimed is:

1. A membrane-free perfusion catheter system comprising:
   a catheter structure formed by an exchange surface having a filament structure;
   a delivery unit for delivery of perfusion fluid to a lumen of the filament structure in a manner to allow for a bidirectional exchange of substances between a medium surrounding the lumen and the perfusion fluid via the filament structure; and
   a drain unit for draining the medium surrounding the exchange surface or for draining the perfusion fluid delivered to the lumen of the filament structure after the exchange of substances between the medium surrounding the lumen and the perfusion fluid via the filament structure;
   wherein a one dimensional extension of gaps formed between filaments of the filament structure is larger than 1 µm;
   wherein at least one of the delivery unit and the drain unit comprises a fluid transport unit for transporting the fluid through the lumen of the filament structure with a flow rate in a range between 0.1 µl/minute and 10 µl/minute.

2. The catheter system of claim 1, wherein the filament structure is adapted in such a manner that filament material of the filament structure is impermeable and gaps between adjacent portions of the filament material are permeable.

3. The catheter system of claim 1, wherein the filament structure comprises an electrically conductive material configured such that an electric signal is applyable to the filament structure to function as an electrode.

4. The catheter system of claim 1,
   comprising a fitting element;
   wherein the filament structure comprises a material connected to the fitting element.

5. The catheter system of claim 1, comprising an impermeable coating covering a first portion of the filament structure, wherein a second portion of the filament structure is free of the impermeable coating.

6. The catheter system of claim 5, wherein the filament structure has a tubular shape having an inner surface and an outer surface, the impermeable coating covering a part of the outer surface.

7. The catheter system of claim 1, wherein the filament structure is arranged in such a manner that the exchange surface is formed at least partially by friction between different portions of the filament structure.

8. The catheter system of claim 1, comprising at least one further exchange surface each having a further filament structure and being arranged to form a multi-lumen arrangement in combination with the filament structure.

9. The catheter system of claim 1, wherein the exchange surface has a deterministic, well-defined size of gaps between the filaments.

10. The catheter system of claim 1, wherein the delivery unit comprises a perfusion fluid container containing the perfusion fluid and being in fluid communication with the lumen of the filament structure.

11. The catheter system of claim 1, wherein the drain unit comprises a fluid collector collecting tissue medium or the perfusion fluid after the exchange of substances between the surrounding medium and the perfusion fluid via the filament structure.

12. The catheter system of claim 1, wherein the exchange surface provided by the filament structure is arranged in a single homogeneous layer.

13. The catheter system of claim 1, wherein the drain unit comprises an analysis unit adapted for analyzing effluent fluid to thereby derive information regarding the medium surrounding the lumen.

14. The catheter system of claim 1, wherein the delivery unit is connected to a first end portion of the exchange surface, and the drain unit is connected to a second end portion of the exchange surface.

15. The catheter system of claim 1, wherein a one dimensional extension of gaps formed between the filaments is larger than 10 µm.

16. A method comprising:
    providing a membrane-free perfusion catheter system with a catheter having an exchange surface formed by a filament structure;
    delivering a perfusion fluid to the catheter in a manner to allow for a bidirectional exchange of substances between a medium surrounding the catheter and the perfusion fluid via the exchange surface;
    draining the medium surrounding the exchange surface or draining the perfusion fluid delivered to the lumen of the filament structure after the exchange of substances between the medium surrounding the lumen and the perfusion fluid via the filament structure; and
    transporting the fluid through the lumen of the filament structure with a flow rate in a range between 0.1 µl/minute and 10 µl/minute by a fluid transport unit of at least one of the delivery unit and the drain unit;
    wherein a one dimensional extension of gaps formed between filaments of the filament structure is larger than 1 µm.

17. The method of claim 16, wherein the method further comprises using the catheter system for measuring at least one physiological parameter.

18. A method of manufacturing a membrane-free perfusion catheter system, the method comprising:
- forming an exchange surface of the catheter based on a filament structure;
- coupling a delivery unit for delivery of perfusion fluid to a lumen of the filament structure in a manner to allow for a bidirectional exchange of substances between a medium surrounding the lumen and the perfusion fluid via the filament structure;
- coupling a drain unit to the filament structure for draining the medium surrounding the exchange surface or for draining the perfusion fluid delivered to the lumen of the filament structure after the exchange of substances between a medium surrounding the lumen and the perfusion fluid via the filament structure; and
- transporting the fluid through the lumen of the filament structure with a flow rate in a range between 0.1 µl/minute and 10 µl/minute by a fluid transport unit of at least one of the delivery unit and the drain unit;
- wherein a one dimensional extension of gaps formed between filaments of the filament structure is larger than 1 µm.

19. The method of claim 18, comprising removing material of an impermeable coating covering the filament structure to thereby expose a portion of the filament structure from the impermeable coating.

* * * * *